United States Patent
Göbel

(10) Patent No.: US 6,526,977 B1
(45) Date of Patent: Mar. 4, 2003

(54) TRACHEAL BREATHING APPARATUS

(76) Inventor: Fred G. Göbel, Blumenstrasse 30, D-69115 Heidelberg (DE)

(*) Notice: Subject to any disclaimer, the term of this patent is extended or adjusted under 35 U.S.C. 154(b) by 0 days.

(21) Appl. No.: 09/446,845
(22) PCT Filed: Feb. 23, 1999
(86) PCT No.: PCT/EP99/01175
§ 371 (c)(1), (2), (4) Date: Mar. 16, 2000
(87) PCT Pub. No.: WO99/45991
PCT Pub. Date: Sep. 16, 1999

(30) Foreign Application Priority Data

| Mar. 9, 1998 | (DE) | 298 04 142 U |
| Jun. 15, 1998 | (DE) | 198 26 547 |
| Oct. 2, 1998 | (DE) | 198 45 415 |

(51) Int. Cl.[7] ............ A61M 16/00; A62B 9/06
(52) U.S. Cl. ............ 128/207.14; 128/207.15; 604/103.06; 604/103.07; 604/103.14
(58) Field of Search ........ 128/207.14, 207.15, 128/207.16, 207.18; 204/103.06, 103.07, 103.14

(56) References Cited

U.S. PATENT DOCUMENTS

| 3,481,339 A | 12/1969 | Puig |
| 3,610,247 A | 10/1971 | Jackson |
| 3,638,655 A | * 2/1972 | Doherty ............ 128/207.14 |
| 3,640,282 A | 2/1972 | Kamen et al. |
| 3,669,098 A | 6/1972 | Takahashi |
| 3,766,927 A | 10/1973 | Jackson |
| 3,810,474 A | 5/1974 | Cross |
| 3,818,515 A | 6/1974 | Neville |
| 3,848,605 A | 11/1974 | Harautuneian et al. |
| 3,901,246 A | 8/1975 | Wallace |
| 3,948,273 A | * 4/1976 | Sanders ............ 128/207.14 |
| 3,964,488 A | 6/1976 | Ring et al. |
| 4,018,231 A | 4/1977 | Wallace |
| 4,020,849 A | 5/1977 | Jackson |
| 4,091,816 A | * 5/1978 | Elam ............ 128/207.14 |

(List continued on next page.)

FOREIGN PATENT DOCUMENTS

| DE | 22 46 526 | 11/1980 |
| DE | 39 21 524 | 1/1991 |
| DE | 41 15 497 | 11/1992 |
| DE | 43 34 037 | 4/1995 |
| DE | 196 38 935 | 3/1998 |

OTHER PUBLICATIONS

Colin F. MacKenzie et al., "The Shape of the Human Adult Trachea", The American Society of Anesthesiologists, Inc., Jul. 1978, pp 48–50, vol. 49, No. 1.

(List continued on next page.)

Primary Examiner—Aaron J. Lewis
Assistant Examiner—Joseph F. Weiss, Jr.
(74) Attorney, Agent, or Firm—Burns, Doane, Swecker & Mathis, L.L.P.

(57) ABSTRACT

The present invention relates to a tracheal ventilating device, especially a tracheal tube or tracheal cannula which obturates the trachea as hermetically as possible for ventilating a patient, the device comprising a cuffed balloon which blocks the trachea below the glottis and through which a ventilating cannula is passed, with the cuffed balloon when filled or inflated and freely unfolded without any limitation, being larger than when placed in the trachea in an inflated state, and being made from a soft flexible foil material. To intubate a patient with said device as gently as possible at low pressures over a long period of time and with a low risk of infection, the invention suggests that the draped fold of the cuffed balloon should rest on the trachea and be designed in such a way that the loop created at the dead end of a fold has a small diameter which inhibits the free flow of secretion through the loop of said fold.

25 Claims, 7 Drawing Sheets

U.S. PATENT DOCUMENTS

| | | | |
|---|---|---|---|
| 4,141,364 A | * 2/1979 | Schultze | 128/207.14 |
| 4,156,428 A | 5/1979 | Henkin | |
| 4,235,239 A | 11/1980 | Elam | |
| 4,423,725 A | 1/1984 | Baran et al. | |
| 5,038,777 A | * 8/1991 | Dunn | 128/207.14 |
| 5,049,131 A | * 9/1991 | Deuss | 604/96 |
| 5,247,927 A | 9/1993 | Kepp et al. | |
| 5,305,740 A | * 4/1994 | Kolobow | 128/207.14 |
| 5,322,062 A | * 6/1994 | Servas | 128/207.14 |
| 5,398,692 A | 3/1995 | Hickey | |
| 5,403,280 A | * 4/1995 | Wang | 604/96 |
| 5,520,174 A | 5/1996 | Evans et al. | |
| 5,531,905 A | 7/1996 | Dobrez et al. | |
| 5,546,936 A | 8/1996 | Virag et al. | |
| 5,638,813 A | 6/1997 | Augustine | |
| 5,653,230 A | 8/1997 | Ciaglia et al. | |
| 5,693,014 A | * 12/1997 | Abele et al. | 604/96 |
| 5,746,745 A | * 5/1998 | Abele et al. | 606/108 |
| 5,765,559 A | * 6/1998 | Kim | 128/207.15 |
| 5,833,915 A | 11/1998 | Shah | |
| 5,873,362 A | * 2/1999 | Parker | 128/207.14 |
| 6,010,480 A | * 1/2000 | Abele et al. | 604/96 |

OTHER PUBLICATIONS

M. Oikkonen et al., "Leakage of fluid around low–pressure trachael tube cuffs", Anaesthesia, 1997, vol. 52, pp. 567 569.

C.F. MacKenzie et al. "A Study of Inflatable Cuffs on Endotrachael Tubes", British Journal of Anaesthesia, 19/6, pp. 105–109.

C.F. MacKenzie et al., "Human trachael circumference as an indicator of correct cuff size", Anesthesiology, vol. 83, No. 3, Sep. 1980, p. 414.

Flavin et al, "Failure of a High–Compliance Low–pressure Cuff to Prevent Aspiration," *Anesthesiology*, vol. 12, No. 2, Feb. 1975, pp. 216–219.

Crawley et al., "Tracheal Cuffs," *Anaesthesia*, vol. 30, 1975, pp. 4–11.

Bernhard et al., "Adjustment of Intracuff Pressure to Prevent Aspiration," *Anesthesiology*, vol. 50, No. 4, Apr. 1979, pp. 363–366.

Macrae et al., "Aspiration around high–volume, low–pressure endotrachael cuff," *British Medical Journal*, vol. 283, Nov. 7, 1981, p. 1220.

Mehta, S., "Aspiration around high–volume, low–pressure endotracheal cuff," *British Medical Journal*, vol. 284, Jan. 9, 1982, pp. 115–116.

Lomholt et al., "A New Tracheostomy Tube," *Acia Anaesth. Scand.*, vol. 25, 1981, pp. 407–411.

Seegobin et al., "Endotrachael cuff pressure and tracheal mucosal blood flow: endoscopic study of effects of four large volume cuffs," *British Medical Journal*, vol. 288, Mar. 31, 1984, pp. 965–968.

Seegobin et al., "Aspiration beyond endotracheal cuffs," *Canadian Anaesthetists' Society Journal*, vol. 33, No. 3, 1986, pp. 273–279.

Petring et al., "Prevention of Silent Aspiration Due to Leaks around Cuffs of Endotracheal Tubes," *Anest. Analg.*, vol. 65, 1986, pp. 777–780.

Young et al., "Leakage of fluid past the tracheal tube cuff in a benchtop model," *British Journal of Anaesthesia*, vol. 78, 1997, pp. 557–562.

Young et al., "Evaluation of a new design of tracheal tube cuff to prevent leakage of fluid to the lungs," *British Journal of Anaesthesia*, Vo. 80, 1998, pp. 796–799.

Young et al., "Prevention of tracheal aspiration using the pressure–limited tracheal tube cuff," *Anaesthesia*, vol. 54, 1999, pp 559–563.

\* cited by examiner

TRACHEAL BREATHING APPARATUS

The present invention relates to a tracheal ventilating device, especially a tracheal tube or tracheal cannula which obturates the trachea as hermetically as possible for ventilating a patient, the device comprising a cuffed balloon which blocks the trachea below the glottis and through which a ventilating cannula is passed, the cuffed balloon when filled or inflated and freely unfolded without any limitation, being larger than when placed in the trachea in an inflated state, and being made from a soft flexible foil material.

In a tracheal tube of such a type as is known from DE 196 38 935, it is suggested that a foil-like, extremely expandable material should be used for the cuffed balloon, the material closely nestling on the trachea or the local structures of the subglottic larynx. To optimize the tamponade of the subglottic space, it is recommended that the cuffed balloon should be pre-formed in accordance with the morphology of the space to be filled. An undesired draped fold is thereby to be avoided. It is to be ensured that the foil closely rests on the trachea so that no secretion passes from the pharyngeal space into the lung, if possible. A microaspiration of secretion beyond the cuffed balloon is thereby reduced considerably.

Secretion which passes into the distal trachea-bronchial system is the reason for the development of most of the ventilation-associated pneumonias.

In the tracheal tube suggested in DE 196 38 935, the cuffed balloon is elastically expanded while being inflated, and closely nestles on the wall of the trachea without any draped fold. When the filling pressure of the cuffed balloon exceeds the blood flow pressure of the vascular bed supplying the film of the mucous membrane, serious structural lesions of the epithelium might ensue. Above all with patients intubated for a long period of time, the filling pressure prevailing in the cuffed balloon should be kept at a level which is as low as possible and does not impair mucosal perfusion. By contrast, if the filling pressure is chosen such that it is too low, this might lead to a leakage of bacterially contained pharyngeal secretion beyond the cuffed balloon, resulting in a contamination and infection of pulmonary tissue.

It has therefore been suggested for long-term intubation that use should be made of cuffed balloons which unfold at a moderate filling pressure in the trachea without the cuff coat itself having to be expanded. The diameter of the freely unfolded cuffed balloon is here greater than that of the trachea to be closed. The residual amount of the cuff coat is turned into folds during the tracheal blockage of the cuff. On the other hand, however, it has been found that such cuffs have a high permeability to pharyngeal secretion, which means an increased risk of pneumonia. The leakage of secretion of said cuffed balloons is in the range of milliliters per second, which even corresponds to a macroaspiration in quantitative terms.

Therefore, it must be assumed that conventional cuffed balloons cause most of the pneumonias frequently observed in patients who are ventilated for a long period of time (incidence: 10% to 80%, depending on the respective patient).

It is the object of the present invention to improve a tracheal tube of the above-mentioned type in such a manner that a patient can be intubated as gently as possible at low pressures over a long period of time and that the risk of infection is low.

According to the invention this object is achieved with a tracheal tube of the above-mentioned type which is characterized in that the draped fold of the cuffed balloon rests on the trachea and is designed in such a way that the loop formed at the dead end of a fold has a small diameter which inhibits the free flow of secretion through the loop of the fold.

The sealing capacity of the cuff can thus be improved considerably; the risk of ventilation-associated pneumonia is reduced accordingly.

Surprisingly enough, the flow of secretion can be influenced by a specific design of the cuff folding in the area of the loop of the fold, i.e. at the base of the fold. While in the prior art it has so far been assumed that cuffed balloons with a draped fold cannot rest on the trachea in a sufficiently tight manner because of the low filling pressure, the invention shows a method of inhibiting the flow of secretion, the method being employed in the area of the loop of the fold. When the diameter of the loop is sufficiently small at the base of the fold, the free flow of secretion through the loop is inhibited. When the cuff is blocked, the resultant loops at the deep end of the fold can be reduced with respect to their diameter, for instance by selecting the material or the foil thickness, in such a manner that the flow of secretion is decelerated or, ideally, stopped altogether.

This is surprising because leakage has always been regarded as a problem of pressure. A constructional change in the draped fold has so far not been considered yet.

Preferably, the loop is given a capillary size. This will then result in adequate adhesion forces of the secretion on the loop and in a sufficient viscosity-dependent resistance of the secretion to reduce the flow of secretion. The flow rate in the capilary-sized loop is then smaller than the theoretically possible rate without adhesion or viscosity forces, so that a smaller amount of secretion will flow therethrough in the course of time. In an optimum case the diameter of the loop is made so small that the flow of secretion is stopped altogether.

The diameter of the loop may be less than 0.1 or 0.05 mm in an especially advantageous development. At a value below 0.1 mm a certain inhibition of the flow rate of the secretion through the loop can already be observed. At a loop diameter of less than 0.05 mm, the flow of secretion is further decelerated and almost stopped.

Advantageously, the wall thickness of the foil material can be chosen to be so small that the inner radius of the developing loops is reduced at physiologically tolerated filling pressures to such an extent that the free flow of secretion is prevented. The more flexible and thinner the material is, the smaller is the diameter of the loop.

The wall thicknesses of conventional cuffed balloons predominantly range from 0.06 to 0.1 mm.

It is suggested that the wall thickness of the foil should be slightly smaller than or equal to 0.02 mm. When the cuffed balloon is made from such a foil, the flow of secretion through the loop will already be inhibited at a standard filling pressure.

In a variant of the invention, the wall thickness of the foil is approximately 0.01 to 0.005 mm. In the case of a wall thickness ranging from 0.01 to 0.005 mm, a soft flexible foil will already inhibit the flow of secretion in a satisfactory manner and the stasis thereof will be achieved in the area of the base of the fold, respectively.

Foils of presently available materials having wall thicknesses of less than 0.005 mm are not sufficiently tear-resistant for the cuffed balloon which is designed according to the invention. If suitable and sufficiently resistant materials are available, foil thicknesses below 0.005 mm should be aimed at for achieving optimum sealing characteristics.

According to a preferred embodiment the foil material of the cuffed balloon may e.g. consist of polyethylene teraphthalate (PETP), low-density polyethylene (LDPE), polyvinyl chloride (PVC) or polyurethane (PU). These materials are body-tolerated and, when being processed into correspondingly thin walls, are especially suited for forming a hermetically obturating draped fold. Copolymer admixtures for modifying the characteristics of the material are possible (e.g. LDPE-EVA).

The cuffed balloon possibly consists of a material which adheres to itself and the adhesion of which helps to reduce the clear diameter of a loop at the base of the fold.

In a variant of the invention, the wall thickness of the foil may be thinner in the area of the draped fold than in the fold-free area directly adjacent to the tracheal mucous membrane. Folds are preferably formed in the thin-walled cuff region because the foil can more easily be deformed in said area. The foil base can form loops of a smaller diameter because of the smaller wall thickness. In the more thick-walled cuff region between the folds the cuff coat has characteristics that are slightly more rigid so that it only rests in a rounded form on the wall of the trachea.

In a particular manner the fold walls which are opposite to each other in a fold are interconnected in the area near the base of the fold. The point of connection may be provided directly next to the forming loop so that the size of the loop is set by said point of connection to a desired diameter.

Preferably, the opposite fold walls can be interconnected at the dead end of the fold to fill the loop, whereby the flow of secretion is reliably prevented. It is also possible to weld or glue the opposite fold walls of a fold to each other.

Particularly, a fold section having a variable cross-section in the depth of the fold, in which the opposite fold walls are not materially interconnected, may be adjacent in the fold to the connection portion of the opposite fold walls. The cuffed balloon can adjust itself to the trachea in size and shape via such a pre-formed draped fold having a variable fold depth, i.e. in accordance with the concept regarding the residual cuff coat.

In a tracheal tube of said type, which is known from DE 196 38 935, it is suggested that the conventional cuff of the tracheal tube should be supplemented by a second tampon balloon which directly follows the cuff to the oral side and completely fills the so-called subglottic space (space between the upper edge of the cuff and the vocal cords). The tampon balloon consists of a foil-like, extremely expandable material which closely nestles on the local structures of the subglottic space under expansion. To optimize the tamponade of the subglottic space, it is recommended that the balloon should be pre-formed in accordance with the morphology of the space to be filled. A fold-free surface of the tampon balloon which is as smooth as possible is to prevent any accumulation of secretion and the formation of a subglottic germ reservoir, respectively.

However, the expansion of such a displacement body is accompanied, above all in the region of the morphologically complicated inner larynx, with the formation of pressure peaks in the area of prominent structures that extend into the local space. When the filling pressure of the tampon balloon exceeds the perfusion pressure of the vascular bed supplying the film of the mucous membrane, serious lesions of the wall structures may ensue, above all in the region of the dorso-lateral subglottic larynx.

To prevent the larynx from being damaged by pressure, it is recommended that the tampon balloon should also be provided with a residual volume, i.e., its volume in the freely unfolded state should exceed the volume of the inner larynx to be filled. The tampon balloon complies with the inventive principles governing the design of a sealing and gentle cuffed balloon. The formation of the above-described capillary-like structure is thereby prevented.

Since a lot of applications require a reliable and mechanically loadable anchorage of the tracheal tube within the windpipe, a certain minimum wall thickness of the fixing cuff must not be exceeded, depending on the respective quality of the material. Despite a substantial reduction of the wall thickness, the formation of fluid-draining loops cannot adequately be prevented in all cases.

Nevertheless, in order to ensure optimum sealing characteristics, the present invention suggests that the mechanically fixing cuff should be supplemented by an additional sealing tampon balloon complying with the above-described principles of design that govern sealing aspects and tissue compatibility. The tampon balloon can be subjected to a minimum filling pressure of preferably 10 to 15 mbar which has only the function to unfold the thin, sealing balloon wall.

As for its arrangement and relation with respect to the tube shaft or the fixing cuff, the tampon balloon may correspond to the embodiments described in DE 196 38 935.

It is suggested that the fixing cuff should be mounted at the caudal side of the device, and the tampon balloon relative thereto at the cranial side. During intubation the fixing cuff is pushed forwards beyond the cricoid cartilage of the larynx, preferably into the region of the middle tracheal third where it is anchored in a reliable and tracheally compatible manner. The tampon balloon which is arranged at the cranial side relative thereto can expand in the direction of the subglottic space where, being arranged upstream of the fixing cuff, it obturates secretion seeping from the pharynx.

The fixing cuff and the tampon balloon may also be positioned in sequential order on the ventilating cannula. The tampon balloon while expanding to the cranial side can partly cover the so-called subglottic space up to the glottic plane or slightly beyond said plane. Since both balloons are filled separately via corresponding supply lumina mounted inside the tube shaft, the functions of fixing cuff and tampon balloon in the case of a serial arrangement can largely be controlled independently of each other.

Preferably, the point of connection between the two serially arranged balloons is configured such that no secretion can accumulate in the area thereof in the filled and tracheally unfolded state.

Advantageously, the fixing cuff can be enclosed by the tampon balloon at least in portions, preferably completely. The outer tampon balloon can thus expand to the caudal side up into a variable area of the fixing cuff. The formation of a germ reservoir between the balloons is thereby prevented.

In a preferred variant, the cuff which tracheally fixes the tube is entirely surrounded by the tampon balloon. The tampon balloon extends from the caudal end via the cranial end of the cuff into the so-called subglottic space and into the area of the vocal cord plane or slightly beyond said plane. In this interposed embodiment regarding the combination of a fixing cuff with a tampon balloon, the invention suggests a particular mode of handling.

After conventional intubation the outer liquid-obturating tampon balloon is initially to be filled and is to nestle on the wall of the local space to be filled at a minimum pressure. Subsequently, the fixing cuff arranged in the interior is then unfolded in the customary manner and at the standard filling pressures for stabilizing the tube in the trachea. Hence, the fixing cuff has no fluid contact, i.e., the possible formation of loops in the coat of the inner cuff has no fluid-draining effect.

To prevent the two balloons from adhering to each other while unfolding, and to ensure their independent mechanical characteristics during ventilation, it is suggested that a small amount of a separating medium, such as oil or talcum, should be introduced into the space between the balloons.

When the tampon balloon which is subjected to a minimum pressure that is gentle on the tissue is expanded into the region of the glottis or slightly beyond said region, the potential path of entry for germ-containing secretion is extended to a maximum. The volume of secretion is reduced by the displacing tampon balloon to a small film exposed to the epithelium-inherent defense factors and is thus reduced with respect to its flow rate to a maximum degree. On the whole, the efficiency of the local defense mechanism is thereby optimized considerably.

Since the stasis of germ-containing material above the tracheally fixing cuff is suppressed virtually completely, changes in the mucous membrane due to chronic inflammation can additionally be prevented.

When the tampoon balloon extends beyond the vocal cords into the supraglottic region, the permanently traumatized contact of the tube shaft with the vocal cords can be reduced by the tension-free lining of the vocal cords with the coat of the tampon balloon.

Every conventional tube (high-volume/low-pressure, high-pressurellow-volume cuff or intermediarily designed cuff) that does not, as preferred above, eliminate the subglottic germ reservoir can be optimized with respect to tightness and tissue compatibility by the interposed arrangement of the fixed cuff and by a tampon balloon having a wall thickness of only a few micrometers. The outer tampon balloon should only slightly exceed the fixing cuff as to its cranial and caudal extension or should dimensionally correspond to the fixing cuff. The two balloons can be filled separately. In this case, too, the outer, hermetically obturating cover which has a thickness of only a few micrometers is to prevent by way of its initial unfolding that the formation of fluid-conducting tubuli of the inner cuff with the greater wall thickness causes a leakage of secretions.

Such an arrangement of a sealing and stabilizing coat or envelope makes the invention applicable not only to tracheal tubes, but also in particular to tracheal cannulas. Tracheal cannulas are inserted not via the larynx, but via a surgically laid opening (stoma) in the windpipe.

The maintenance of the filling pressure in all of the above-described cuff and tampon balloons is ensured by an extracorporeally mounted reservoir. In accordance with the Lanz principle, such reservoirs may be equipped with a self-regulating valve mechanism, or may be designed in the manner of simple valve-carrying reservoir balloons.

To be able to estimate the desired filling pressure, an imprinted figure or a specific form of the reservoir balloon may be chosen which specifically varies in a corresponding filling state.

To prevent pressure variations inside the trachea or the larynx from effecting an expansion of the wall structures, the material compliance of the reservoir balloon should not exceed that of the cuff or tampon balloon.

The supply legs leading to the tampon balloon should be chosen such that they have a sufficiently large lumen so as to effect a rapid pressure compensation.

Any suitable fluid may be used for filling the sealing or fixing cuffed balloons.

Moreover, when liquids are used, a valve mechanism can be dispensed with and the filling operation can solely be controlled via an open liquid column.

The inventive seal of the tracheal or laryngeal remaining lumen (which is created during intubation) by way of a reduction of the wall thickness of the cuff coat to the range of a few micrometers also permits the liquid-tight tamponade of the intubated trachea of neonates, babies or infants.

On account of the high tissue vulnerability with respect to conventionally cuffed balloons, all kinds of sealing devices have so far been dispensed with during intubation. A tissue-compatible, liquid- or gas-tight sealing of the extremely sensitive upper airways would be possible by way of an elongated tampon balloon which fills the trachea and the larynx and is subjected to minimum pressures (preferably of 5 mbar).

Embodiments of the invention are shown in the drawings and will now be explained:

Figure 1:
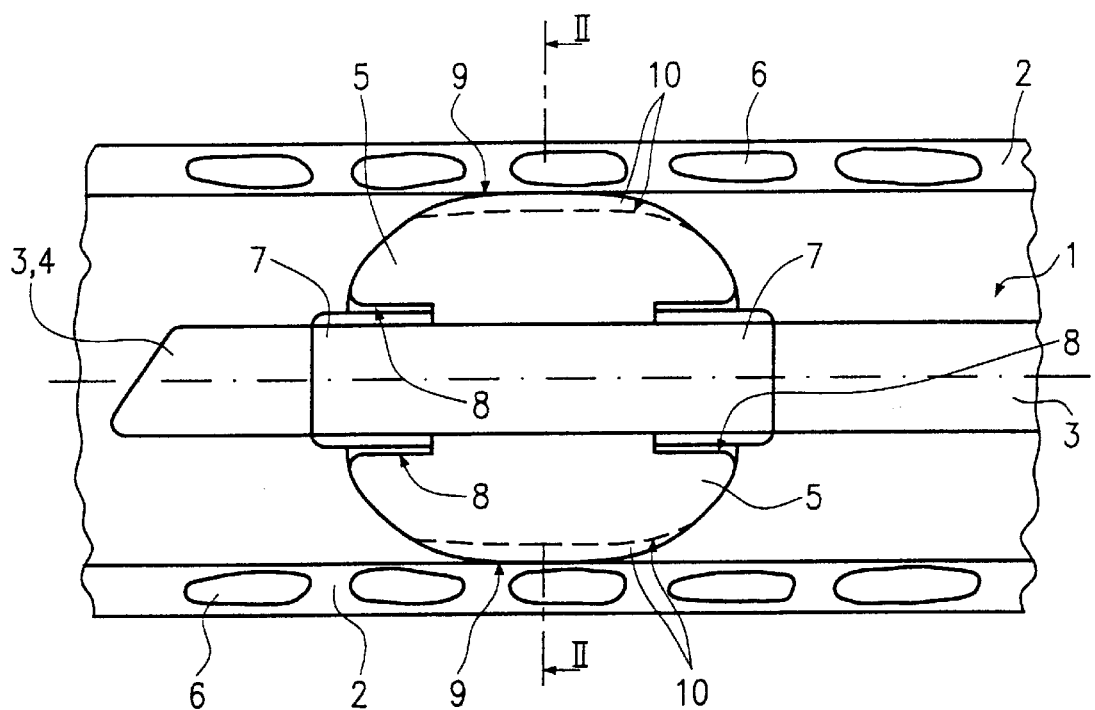
FIG. 1 is a longitudinal section through the wall of a trachea with a tracheal tube placed therein, in accordance with a first embodiment of the invention.

FIG. 1 shows a first embodiment of an inventive tracheal tube 1 or tracheal ventilating device which is placed in a trachea 2. A hollow ventilating cannula 3 terminates at its caudal end 4 at an inclined angle relative to its longitudinal axis. At the caudal end 4, respiratory air enters into and exits from the lung. The ventilating cannula 3 is led (not shown) via the larynx and the pharyngeal space out of the patient's mouth and is there connected to suitable ventilating devices (not shown).

A cuffed balloon 5 is mounted on the ventilating cannula 3 near the caudal end 4. The ventilating cannula extends through the cuffed balloon. The tube I is inserted into the trachea 2 in such a manner that the cuff 5 comes to rest in the region of the middle trachea. Of the trachea, tracheal rings 6 are outlined.

The cuff 5 has about the shape of a balloon and surrounds the ventilating cannula 3 approximately in the manner of a tube or hose. It is secured at two spaced-apart ends 7 to the ventilating cannula 3, e.g. by bandaging, shrinking, welding or sealing or gluing, so that the secured end 7 of the balloon 5 rests on the cannula 3 in fluid-tight fashion.

The cannula 3 can be filled via a connection (not shown in FIG. 1) with fluid at a desired pressure.

In the area of the secured ends 7, a bent fold 8 is provided on the balloon and extends in ring-like fashion around the ventilating cannula 3. The bent fold 8 allows for adequate axial movements of the cuffed balloon 5 and the ventilating cannula 3 relative to one another without the contact surface of the cuffed balloon 5 on the trachea 2 being affected in a medicinally adverse manner.

FIG. 1 shows the cuffed ballon 5 in its inflated or filled condition and placed within the trachea. The filling pressure is about 20 to 30 mbar (preferably 25 mbar). If the cuffed balloon 5 was not placed in the trachea, it would unfold in its completely filled state beyond the tracheal diameter. When placed in the trachea, it circumferentially rests with a contact surface 9 on the inside of the trachea 2. The residual cuff is turned in predominantly radially inwardly oriented folds 10.

The material of the cuffed balloon 5 consists of a soft flexible foil material preferably having a wall thickness of less than 0.02 mm; the optimum thickness, however, is 0.01 to 0.005 mm or even below 0.005 mm. The foil material is body-tolerated and consists, e.g., of polyethylene teraphthalate (PETP), low-density polyethylene (LDPE), polyvinyl chloride (PVC) or polyurethane (PU).

At a clinically standard filling pressure of 25 to 30 mbar, the foil is not stretched, or is only stretched to a minimum degree, but is flexibly bent. It rests on the trachea 2 with folds 10. In FIG. 1, the fold areas are outlined in broken lines. The folds are normally arranged to be axial to the trachea 2 and to the ventilating cannula 3. Most of them are oriented in the longitudinal direction in parallel with the tube shaft 3. The wall thickness of the foil is preferably thinner in the area of the formation of the folds 10 than in the fold-free area of the contact surface 9.

Optionally, the selected filling pressure of the cuffed balloon may range from 10 to 30 mbar.

Figure 2:
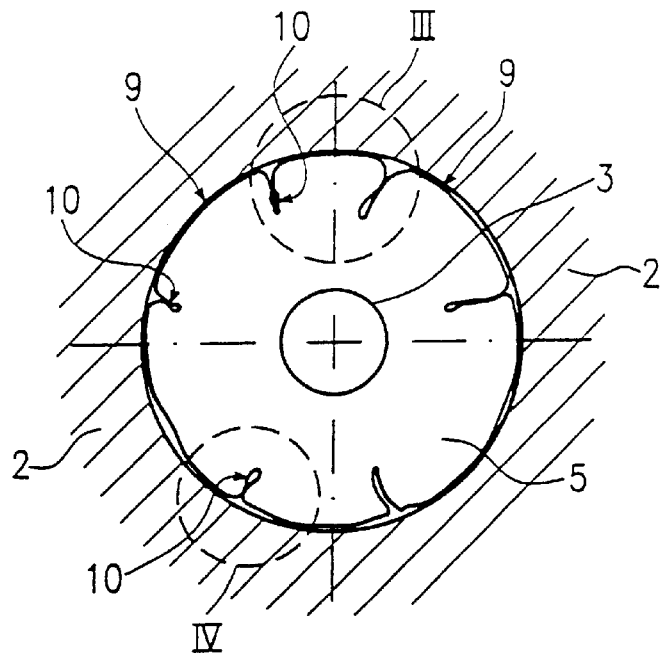
FIG. 2 is a cross-sectional view along the sectional line II—II in FIG. 1.
Figure 3:
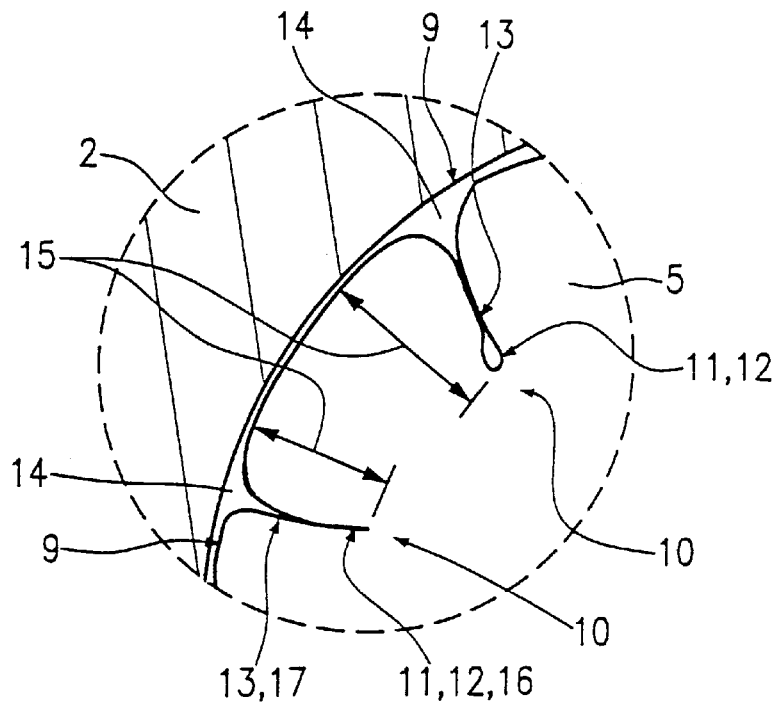
FIG. 3 is an enlarged view showing detail III of FIG. 2.
Figure 4:
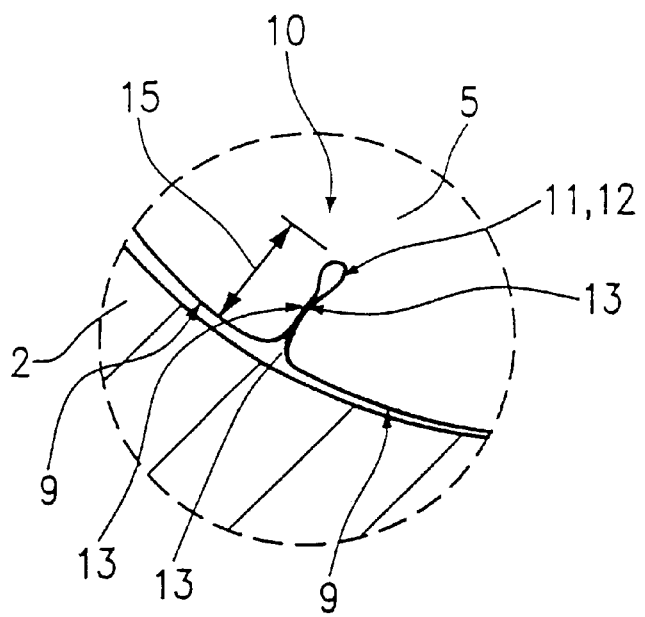
FIG. 4 is an enlarged view showing detail IV of FIG. 2.

FIG. 2 is a cross-sectional view taken along the sectional line II—II of FIG. 1; reference is here made to the description of FIG. 1 with respect to parts having identical reference numerals. FIG. 2 shows how in the filled state of the cuffed balloon 5 the folds 10 are formed, projecting approximately radially inwards. The folding results from the diameter of the cuffed balloon 5 which in the freely unfolded state is greater than the cross-section of the trachea 2 to be filled. Each of the folds 10 is provided at its end, i.e. at the fold base 11, with a loop 12 which is obtained by the cuff coat being turned over in said area. Reference is here made to FIGS. 3 and 4 which show the folds 10 on an enlarged scale. As for like reference numerals, reference can be made to the above description of the figures.

According to FIGS. 3 and 4 each of the folds 10 consists of two fold walls 13 which are opposite in parallel fashion and which are in body contact with each other or are separated from each other by a thin secretion film. In the last-mentioned case the secretion film forms a certain adhesive layer between the two fold walls 13. The two fold walls jointly form a fold web. The fold web is normally oriented from the contact surface 9 of the balloon radially inwards.

While the folds are being formed, a small clear gore 14 in which secretion is collected at a small amount is created between the trachea 2 and the inwardly extending fold walls 13. Even in the case of cuffed balloons having an increased wall thickness, said gore 14 only releases a small lumen as the fold walls must only be bent by about 90° in said area. In vivo it is obturated to a large extent by the soft tracheal mucosa which already prolapses into the gore at a low contact pressure. The contact pressure required for obturating said gore 14 can be further reduced by using very thin-walled cuff materials.

While a loop 12 which forms fluid-conducting capillaries is created at the fold base in the case of cuffed balloons having a conventional wall thickness (about 0.06 mm to 0.1 mm), a turned fold 12 is formed when very thin foils are used according to the invention for constructing cuffed ballons, said turned fold 12 having a diameter which is so small that the free flow of secretion at the fold base is inhibited or blocked altogether. The diameter of the loop of the fold is preferably less than 0.1 or 0.05 mm.

FIG. 3 shows a fold 10 whose opposite fold walls 13 are directly connected to each other by sealing or welding or gluing in the area of the fold base. Hence, there is no loop 12 causing a possible leakage of secretions. The fold section 17 adjoining the connection area 16 is formed by opposite fold walls 13. These are not connected and form the variable fold section, with the depth 15 of the fold adjusting itself to the respective tracheal diameter.

The loop 12 may have a capillary size in the case of which the actual flow rate of the secretion is smaller than the flow rate that is theoretically possible through the free cross-section of the loop without adhesion or viscosity forces. The inhibiting effect of the adhesion or viscosity forces may be so pronounced at a corresponding size of the loop that although the loop 12 is filled with secretion, secretions cannot flow therethrough.

Figure 5:
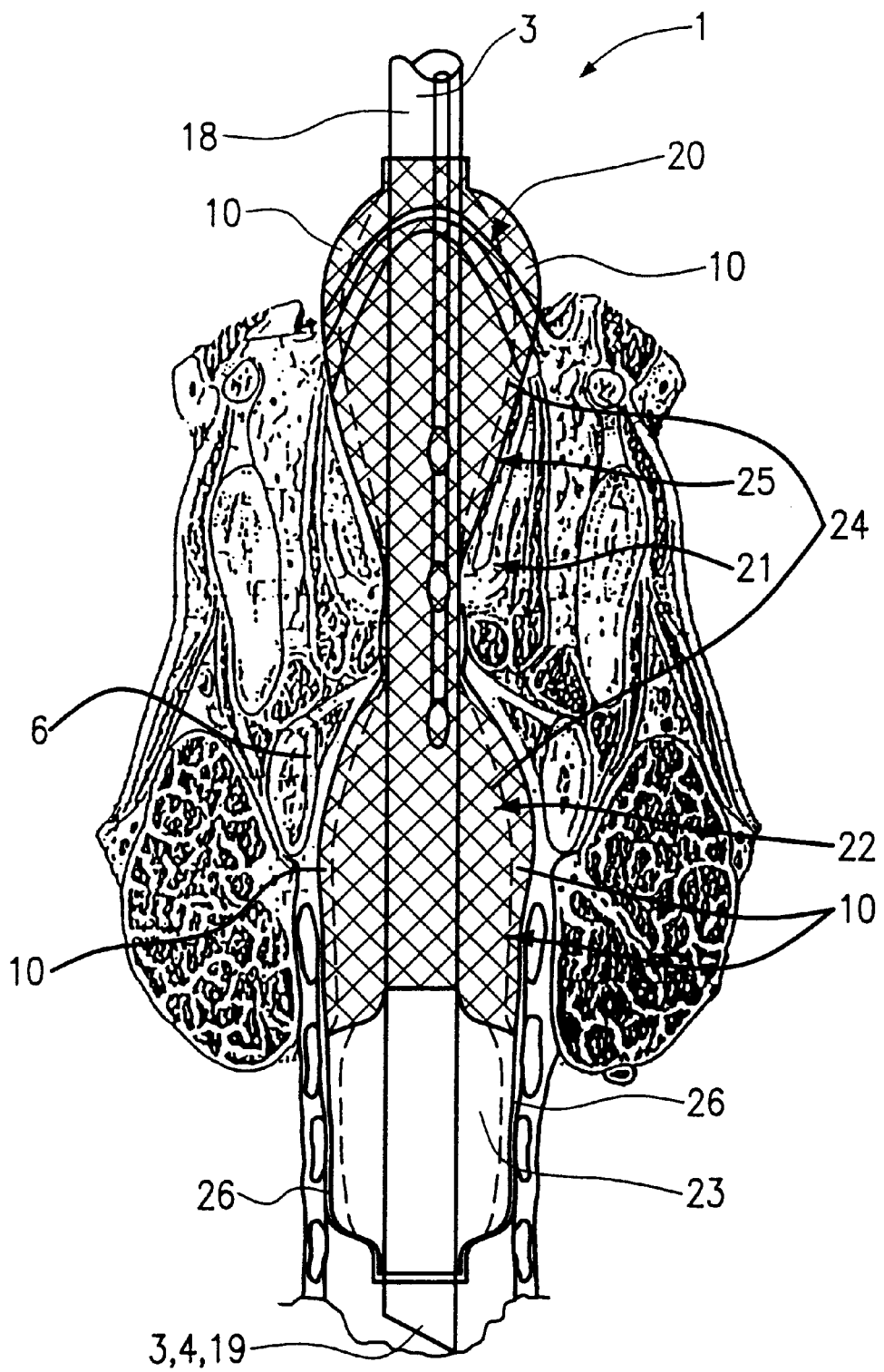
FIG. 5 shows a tracheal tube of the invention according to a second embodiment in a frontal section through a larynx with adjoining anatomical structures.

FIG. 5 shows a second embodiment of an endotracheal tube 1 exhibiting the topographical relationships with the relevant adjoining anatomical structures (larynx and upper windpipe). The tracheal tube passes from the cranial side 18 to the caudal side 19 through the epiglottis 20, the vocal cords (glottis) 21 and the so-called subglottic space 22 which follows the vocal cords towards the caudal side and which is defined by the upper edge of the cuff 23. The tracheal tube is mechanically anchored below the cricoid cartilage 6, preferably, however, in the region of the middle trachea, by way of an air-blocked cuff 23.

The cuff is arranged inside a tampon balloon 24, the tampon balloon and the cuff having separate lumina which can be filled independently of each other. The cuff 23 and the tampon balloon 24 closely rest on each other in the filled state.

The tampon balloon 24 optionally extends up to the subglottic space 22, the glottic plane 21 or slightly therebeyond into the supraglottic region 25.

The cuff 23 need not necessarily be arranged inside the tampon balloon 24. It can also be arranged in sequential order (towards the cranial side) on the tube, but in the filled state it should advantageously be in direct tight contact to prevent the formation of a reservoir for germs in the area between the balloons. To this end the balloons may be permanently connected to each other in the joint contact region.

Three variants of design are possible in the area of the support surface 26 of the cuff 23 on the tampon balloon 24. Cuff 23 and tampon balloon 24 are possibly not connected to each other.

Furthermore, the two balloons may be glued or welded to each other in the joint support surface 26 within a variable distal section (e.g. distal third or distal half). The gluing or welding of the joint distal support surface 26 is meant to prevent the thin-walled tampon balloon from herniating to the caudal side or to prevent the debris thereof from turning to the caudal side upon rupture of the tampon ballon and from forming a valve-like mechanism at the caudal end 4 of the ventilating cannula. Finally, both balloons may be glued to each other in the area of the whole common support surface by functional analogy with the sequential arrangement.

The tampon balloon 24 is filled with a suitable liquid or gaseous fluid.

The above-described principles governing the design of cuffed balloons that are tight and gentle on the mucous membrane can be applied to the tampon balloon 24 and/or to the fixing cuff 23.

Figure 6:
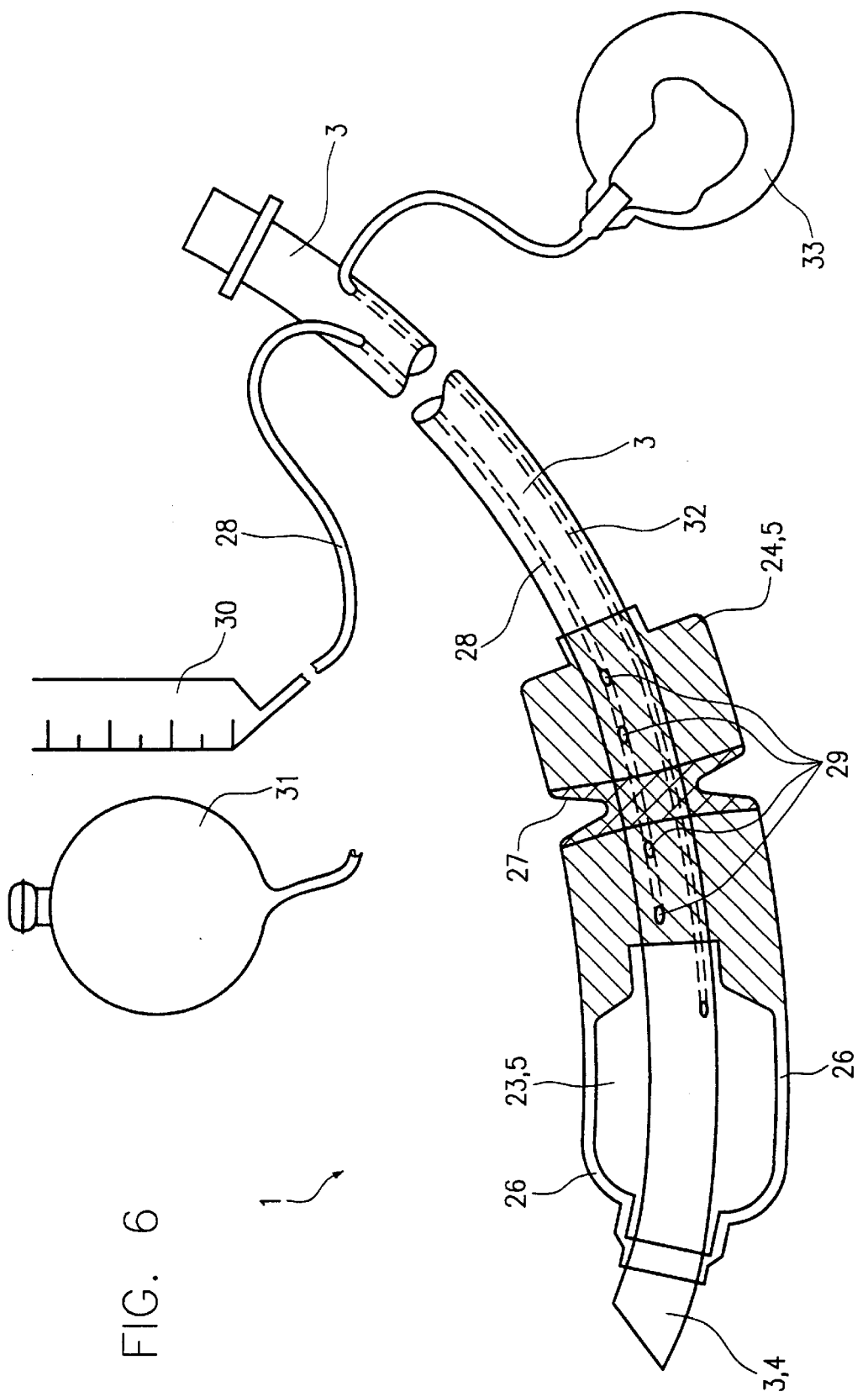
FIG. 6 shows a tracheal tube of the invention according to a third embodiment.

FIG. 6 shows a third embodiment of a tracheal tube according to the invention. The tracheal tube 1 is shown in its filled and freely unfolded state. In contrast to the second embodiment the third embodiment comprises a tampon balloon 24 which in the area of the later vocal cord placement is provided with a preformed incision 27 which corresponds approximately to the anatomical structure of the glottis 21. Preferably, the incision 27 is not expandable or only expandable to a slight degree at the pressures chosen, so that the glottis is not subjected to excessive pressure.

A first passageway 28 which is connected to the tampon balloon 24 via a plurality of exit openings 29 extends within the ventilating cannula 3. The passageway 28 is integrated into the shaft of the tube and is extracorporeally connected to a graduated reservoir, e.g. a water column 30 in the case of liquid filling media. The reservoir, however, may also be designed as an expandable compensating balloon 31 (for liquid or gaseous media). The volume of the compensating balloon 31 should at least correspond to the joint volume of tampon balloon and cuff.

The material of the compensating balloon 31 is preferably slightly more expandable than the material of the tampon balloon 24. Rises in pressure inside the tampon balloon will thus preferably expand the compensating balloon, whereby an expansion of the structures of the larynx can substantially be avoided.

Size and number of the exit openings 29 have been chosen such that a rapid volume displacement is possible between compensatig balloon 31 and tampon balloon 23.

The cuff 23 is connected to a filling balloon 33 via a second passageway 32 which is integrated into the tube shaft. In accordance with the Lanz principle the filling balloon may be equipped with a self-regulating valve mechanism or a simple valve-carrying reservoir balloon.

Figures 7, 8:
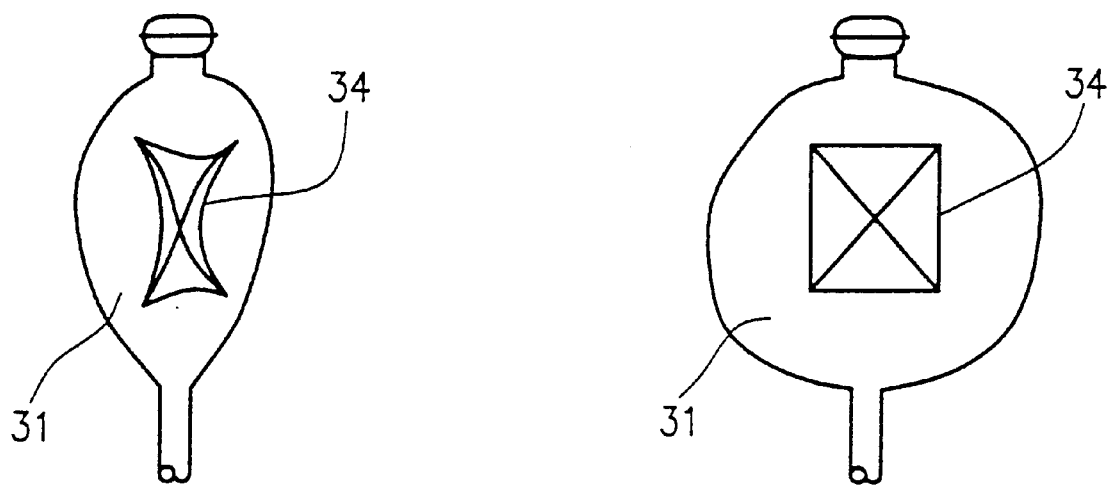
FIG. 7 shows a compensating balloon for a tracheal tube according to the invention, only in a partly inflated or filled state.
FIG 8 shows the compensating balloon of FIG. 7 in an optimally filled state.

FIGS. 7 and 8 show a special embodiment of the compensating balloon 31. In the state shown in FIG. 7, the compensating balloon 31 is not filled so that a pattern 34 printed on the wall thereof assumes an irregular shape. In FIG. 8 the balloon is expanded so that the pattern 34 printed thereon appears in a straight regular shape which is indicative of the optimum filling pressure of the tampon balloon 24.

By analogy, the correct filling pressure inside the tampon balloon could be inferred from a corresponding change in shape of the compensating balloon itself, i.e. from the unfilled to the filled state.

Also possible is a compact interposed arrangement of the two reservoir balloons for the supply of cuffed balloon and tampon balloon in a joint mounting. While the inner balloon which is acted upon with a higher filling pressure is responsible for the fixing cuff, the outer reservoir balloon keeps the tampon balloon in its unfolded state at a moderate filling pressure.

Figure 9:
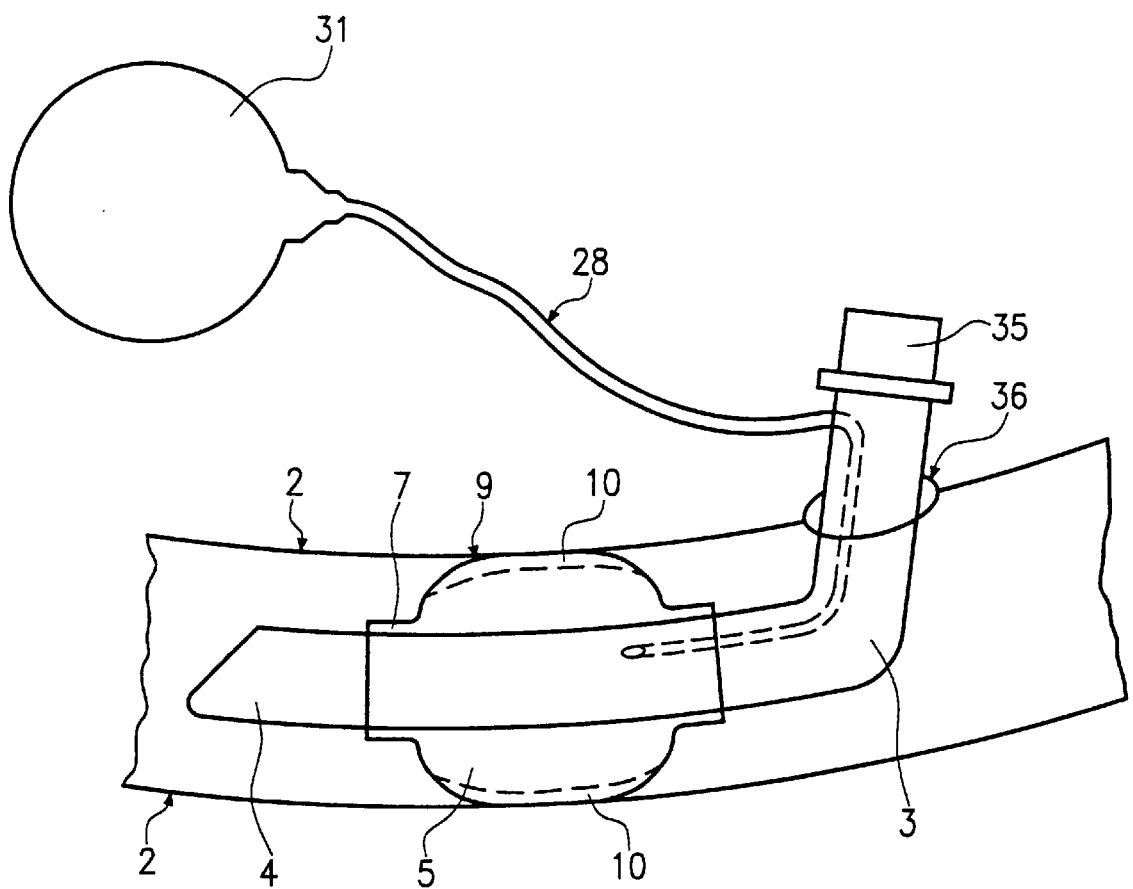
FIG. 9 shows a tracheal cannula of the invention according to a fourth embodiment.

FIG. 9 shows a tracheal cannula 35 as a fourth embodiment of an inventive tracheal ventilating device. It is not introduded via the natural airways, but via a so-called stoma 36 which is surgically provided at the front side of the neck.

The ventilating cannula 3 extends through the stoma 36 and, after having entered into the windpipe 2, it is bent at an approximately right angle to the caudal side. Moreover, the cuffed balloon 5 is formed by analogy with FIGS. 1 to 4, so that reference is made to the previous embodiments with respect to like reference numerals. By analogy, the compensating balloon 31 with the passageway 28 is designed as described with respect to FIG. 6 so that reference is made in this respect to said embodiments.

Figure 10:
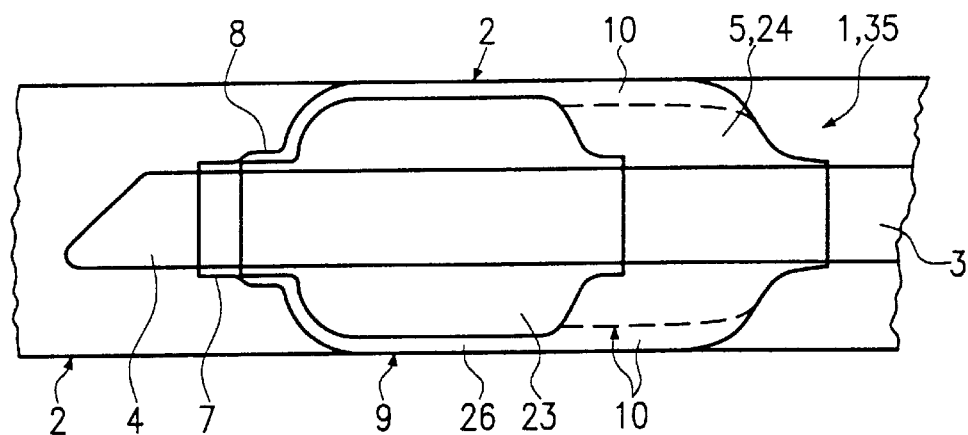
FIG. 10 shows a tracheal tube according to a fifth embodiment.

FIG. 10 shows a fifth embodiment of a tracheal ventilating device which is usable as a tracheal tube 1 or as a tracheal cannula 35. This embodiment corresponds to the embodiment shown in FIG. 5. Like parts are provided with like reference numerals, so that reference is made in this respect to the explanations given for FIG. 5.

In contrast to FIG. 5, the tampon balloon 24 is made shorter in the fifth embodiment shown in FIG. 10 and does not extend into the region of the glottis. As far as its extension is concerned, the balloon is approximately identical with the fixing cuff 23. For reasons of clarity the two separate filling passageways 28 and 29 have not been drawn.

After the cannula has been inserted the outer tampon balloon is primarily filled for sealing purposes. In cases where an additional mechanical stabilization of the tracheal cannula is required, the inner fixing cuff is unfolded in addition. A mutual mechanical influence of the cuff 23 and the tampon balloon 24 is prevented by introducing a separating means between the cuffed balloons. To ensure the sealing of the tracheal cannula, the unfolded state of the tampon balloon is upheld via a communicating, extracorporeally mounted reservoir at a gentle filling pressure of preferably 10 to 15 mbar.

Figure 11:
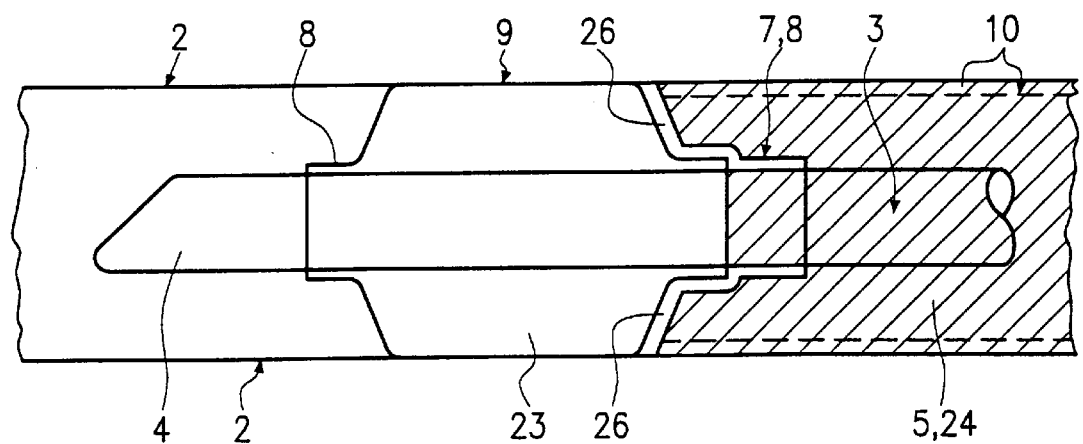
FIG. 11 shows a tracheal ventilating device of the invention according to a sixth embodiment.

FIG. 11 shows a section of a sixth embodiment of a tracheal ventilating device according to the invention. Said embodiment has been developed on the basis of the fifth embodiment according to FIG. 10. Like parts are provided with like reference numerals, so that reference can be made to the explanations given with respect to FIG. 10.

In contrast to the fifth embodiment, the fixing cuff 23 and the tampon balloon 24 are arranged in strict sequential order on the ventilating cannula 3 in the sixth embodiment. On the joint support surface 26 of cuff 23 and tampon balloon 24, the walls thereof are directly adjoining each other so that the formation of a germ reservoir is prevented. The walls in the area of the support surface 26 can selectively be glued or welded to each other.

The operation and function of the embodiments shown in the drawing and regarding an inventive tracheal tube shall now be explained in the following:

During intubation the tracheal tube is pushed forwards beyond the cricoid cartilage of the larynx into the region of the upper tracheal rings so that the cuffed balloon 5 safely comes to rest in the tracheal region. When inflated and freely unfolded without any limitation the cuffed balloon is larger than when placed in the trachea in an inflated state. Placed in the trachea, the draped fold of the cuffed balloon 5 rests on the contact surface 9 of the wall of the trachea.

The cuffed balloon 5 is designed such that at the dead end of a fold 10, a loop 12 is formed with such a small diameter that the flow of secretion is inhibited or stopped altogether.

This is preferably accomplished through the viscosity of the secretion or through the adhesion forces acting within the capillary loop on the secretion.

An aspiration of the secretion can thereby be prevented, as well as the development of a ventilation-associated pneumonia.

The small diameter of the loops 12 can be achieved by using specific flexbile foils of a thickness of only a few micrometers when the cuffed balloon is designed.

Variable regions of the opposite fold walls 13 can also be interconnected, for instance by gluing or welding. Ideally, such a connection of the fold walls 13 is established in the area of the loop 12, thereby preventing any flow of secretion.

The tracheal ventilating device according to the invention can also be used as a stomach probe or tube. The stomach tube is slid into the oesophagus instead of the trachea, a corresponding marking being provided on the tube shaft for positioning the tube. In the oesophagus the cuffed balloon can then be unfolded just as freely, the draped fold of the ballon resting on the wall of the oesophagus without any tension, and loops being formed at the dead end of the developing folds with such a small diameter that said diameter inhibits the free flow of secretions through the loops. This results in a gentle tamponade of the oesophagus which is adapted to the transmural tissue pressure. The tissue of the gullet is not tensed. The instantaneously released lumen of the gullet is just tamponed, resulting in the oesophagus folding. The stomach tube thus provides a seal against rising gastrointestinal secretion in a long-term compatible manner.

Although stomach tubes and tracheal ventilating devices have always been constructed as separate devices up to now and have not been exchangeable with respect to their use, the device according to the invention permits an employment as a tracheal ventilating device and also as a stomach tube. In the case of the stomach tube the ventilating cannula is used as an inner passage-like lumen through which the feeding tube proper can be passed or via which food can directly be supplied.

The stomach tube can also be used in the sense of a so-called Sengstaken-Blakemore tube. In this case the cuffed balloon is also placed in the oesophagus. It is thereby possible to influence the blood flow of the surrounding vessels of the gullet by varying the filling pressure of the cuffed balloon. For instance, the bleeding of surrounding mucosal vessels can be stopped. With the design of the specific above-described unfolding of the residually designed cuff coat, it is also possible to exactly adapt the cuff filling to the necessary vascular occlusion pressure without subjecting the cuff coat and the adjoining structures to any considerable tension. Vascular bleeding can thus be prevented with the minimally required pressure. The mucous membrane of the oesophagus is traumatized to a degree which is as small as possible. When the tube is used as a Sengstaken tube, the inner passage-like lumen serves as a tube shaft. The end of the tube shaft at the stomach side can be designed to be open or closed.

What is claimed is:

1. A ventilating device for obturating a patient's trachea as hermetically as possible, comprising a cuffed balloon which blocks the trachea below a patient's glottis, an air tube, the cuffed balloon being attached to the air tube and being sized to be larger than a tracheal diameter when in a fully inflated state and being made of a sufficiently soft, flexible foil material that forms at least one draped fold in the cuffed balloon when fully inflated in the patient's trachea, wherein the at least one draped fold formed has a capillary size which arrests free flow of secretions across the balloon by virtue of capillary forces formed within the fold to prevent aspiration of the secretions and subsequent infections related to secretion aspiration.

2. The tracheal ventilating device according to claim 1, wherein a capillary diameter of the at least one draped fold is less than 0.1 mm.

3. The tracheal ventilating device according to claim 1, wherein a wall thickness of the foil material is chosen to be sufficiently small such that the free flow of secretion through the at least one draped fold is inhibited in comparison with a theoretical free flow.

4. The tracheal ventilating device according to claim 1, wherein a wall thickness of the foil material is slightly smaller than or equal to 0.02 mm.

5. The tracheal ventilating device according to claim 1, wherein a wall thickness of the foil material is about 0.01 to 0.005 mm.

6. The tracheal ventilating device according to claim 1, wherein a wall thickness of the foil is below 0.005 mm.

7. The tracheal ventilating device according to claim 1, wherein the foil material of the cuffed balloon is made from the group consisting of polyethylene teraphthalate (PETP), low-density polyethylene (LDPE), polyvinyl chloride PVC) or polyurethane (PU).

8. The tracheal ventilating device according to claim 1, wherein a wall thickness of the foil material in an area of the at least one draped fold is smaller than in a fold-free area directly adjoining a patient's tracheal mucosa.

9. The tracheal ventilating device according to claim 1, wherein said fold comprises two opposite fold walls in the at least one draped fold which are interconnected in an area near a base of the at least one draped fold.

10. The tracheal ventilating device according to claim 9, wherein the opposite fold walls at the base of the at least one draped fold are directly interconnected.

11. The tracheal ventilating device according to claim 9, wherein the opposite fold walls of the at least one draped fold are welded or glued to each other.

12. The tracheal ventilating device according to claim 9, wherein a fold section having a variable cross-section in depth is adjacent to an area connecting the opposite fold walls.

13. The tracheal ventilating device according to claim 1, wherein the cuffed balloon consists of a material adhering to itself in the at least one draped fold.

14. The tracheal ventilating device according to claim 1, wherein a tampon balloon formed as the cuffed balloon and a separate fixing cuff adapted to be positioned below the patient's glottis are provided on the air tube.

15. The tracheal ventilating device according to claim 14, wherein the fixing cuff is provided at a caudal side of the device and the tampon balloon is provided relative thereto at a cranial side.

16. The tracheal ventilating device according to claim 14, wherein the fixing cuff and the tampon balloon are arranged approximately in sequential order along the air tube.

17. The tracheal ventilating device according to claim 14, wherein the fixing cuff in a filled state rests directly next to the tampon balloon on a joint support surface.

18. The tracheal ventilating device according to claim 14, wherein a lubricant is provided between the fixing cuff and the tampon balloon.

19. The tracheal ventilating device according to claim 18, wherein the lubricant is provided on a support surface which in a filled state is shared by the tampon balloon and the fixing cuff.

20. The tracheal ventilating device according to claim 14, wherein the tampon balloon and the fixing cuff can be filled separately.

21. The tracheal ventilating device according to claim 14, wherein a size of the tampon balloon in a filled state is designed for filling a patient's subglottic space.

22. The tracheal ventilating device according to claim 14, wherein the tampon balloon is designed to fill both a patient's subglottic and a patient's supraglottic space.

23. The tracheal ventilating device according to claim 14, wherein a shape of the tampon balloon in a filled state differs from a shape of the fixing cuff.

24. The tracheal ventilating device according to claim 14, wherein a wall thickness of the fixing cuff is greater than a wall thickness of the tampon balloon.

25. The tracheal ventilating device according to claim 1, wherein a capillary diameter of the at least one draped fold is less than 0.05 mm.

* * * * *